(12) United States Patent
Walker et al.

(10) Patent No.: US 10,478,632 B2
(45) Date of Patent: Nov. 19, 2019

(54) INTELLIGENT SYNCH MODE FOR DEFIBRILLATION

(71) Applicant: Physio-Control, Inc., Redmond, WA (US)

(72) Inventors: Robert G. Walker, Seattle, WA (US); Fred W. Chapman, Newcastle, WA (US); Isabelle Banville, Newcastle, WA (US); James W. Taylor, Laguna Niguel, CA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 15/989,800

(22) Filed: May 25, 2018

(65) Prior Publication Data

US 2018/0272148 A1 Sep. 27, 2018

Related U.S. Application Data

(63) Continuation of application No. 13/835,261, filed on Mar. 15, 2013, now Pat. No. 9,981,141.

(60) Provisional application No. 61/707,435, filed on Sep. 28, 2012.

(51) Int. Cl.
*A61N 1/39* (2006.01)

(52) U.S. Cl.
CPC ......... *A61N 1/3987* (2013.01); *A61N 1/3931* (2013.01); *A61N 1/3937* (2013.01); *A61N 1/3993* (2013.01)

(58) Field of Classification Search
CPC .. A61N 1/3987; A61N 1/3931; A61N 1/3993; A61N 1/3937
See application file for complete search history.

(56) References Cited

U.S. PATENT DOCUMENTS

| 6,280,461 B1 | 8/2001 | Glegyak et al. |
| 6,405,082 B1 | 6/2002 | Borgenicht |
| 8,036,742 B2 | 10/2011 | Sullivan et al. |
| 2010/0217140 A1 | 8/2010 | Avidor et al. |

FOREIGN PATENT DOCUMENTS

EP  2146630 B1  1/2010

OTHER PUBLICATIONS

Klein, Helmut U. et al., Risk stratification for implantable cardioverter defibrillator therapy: the role of the wearable cardioverter-defibrilliator, European Heart Journal, May 31, 2013, 14 pages, European Society of Cardiology, France.

(Continued)

*Primary Examiner* — Amanda K Hulbert
(74) *Attorney, Agent, or Firm* — McDonnell Boehnen Hulbert & Berghoff LLP

(57) ABSTRACT

The defibrillator may include a heart rhythm detector to detect the heart rhythm of a patient, a manual mode controller structured to set the defibrillator in a synchronous shock operating mode or an asynchronous shock operating mode depending on an input from a human operator, a shock module to cause the defibrillator to deliver a shock to the patient according to the operating mode, and an automatic mode controller structured to, after the shock module has delivered the shock to the patient, set the external defibrillator to the synchronous shock operating mode or the asynchronous shock operating mode depending on the detected heart rhythm of the patient and without input from the human operator.

20 Claims, 9 Drawing Sheets

DEFIBRILLATOR WITH HEART RHYTHM DETECTOR, MANUAL MODE CONTROLLER, AND AUTOMATIC MODE CONTROLLER

(56) References Cited

OTHER PUBLICATIONS

LifeVest System Model WCD 3100 Operator's Manual, 48 pages, ZOLL Lifecor Corporation, Pittsburgh, PA.
LifeVest Model 4000 Patient Manual, 108 pages, ZOLL, Pittsburg, PA.
Klein et al., "Risk stratification for implantable cardioverter defibrillator therapy: the role of the wearable cardioverter-defibrillator." European Heart Journal, May 31, 2013, 12 pages, retrieved from the Internet: Http://eurheartj.oxfordjournals.org/, retrieved on Jun. 17, 2013.

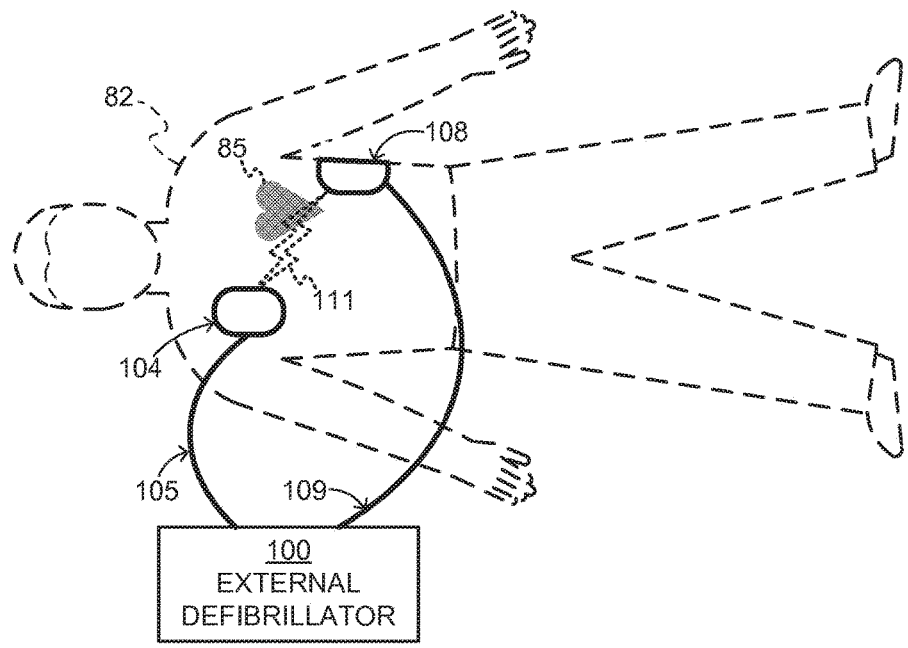
FIG. 1 *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2 *TWO MAIN TYPES OF EXTERNAL DEFIBRILLATORS*

COMPONENTS OF EXTERNAL DEFIBRILLATOR

*DEFIBRILLATOR WITH HEART RHYTHM DETECTOR, MANUAL MODE CONTROLLER, AND AUTOMATIC MODE CONTROLLER*

*HEART RHYTM DETECTOR IMPLEMENTED AS ECG MONITOR*

*HEART RHYTM DETECTOR IMPLEMENTED AS BLOOD PRESSURE MONITOR*

*HEART RHYTM DETECTOR IMPLEMENTED AS PULSATILE BLOOD FLOW MONITOR*

*DEFIBRILLATOR WITH DEFAULT SYNCHRONOUS SHOCK MODE BEFORE SHOCK THERAPY DELIVERED TO PATIENT*

DEFIBRILLATOR WITH DEFAULT SYNCHRONOUS SHOCK MODE BEFORE AND AFTER SHOCK THERAPY DELIVERED TO PATIENT

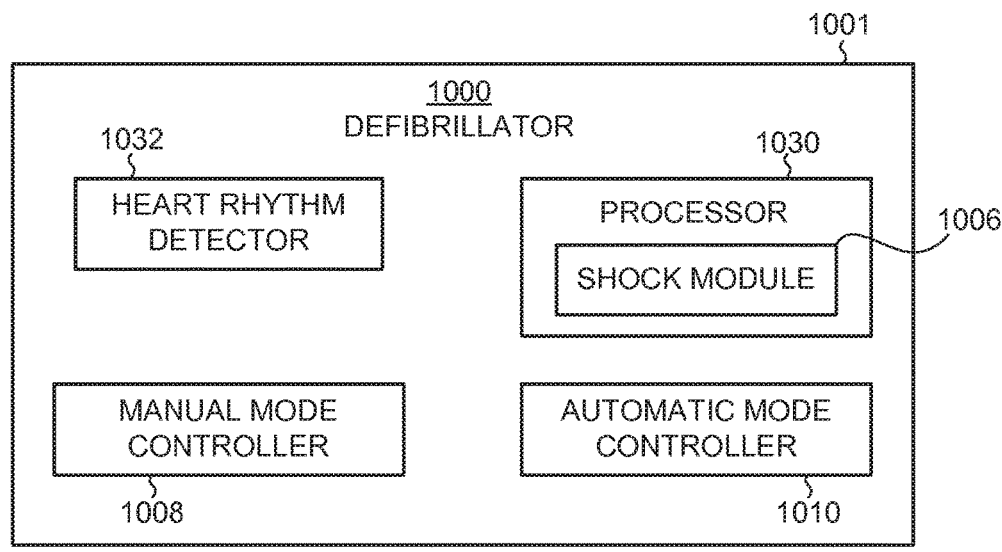
FIG. 10  *DEFIBRILLATOR WITH PROCESSOR*
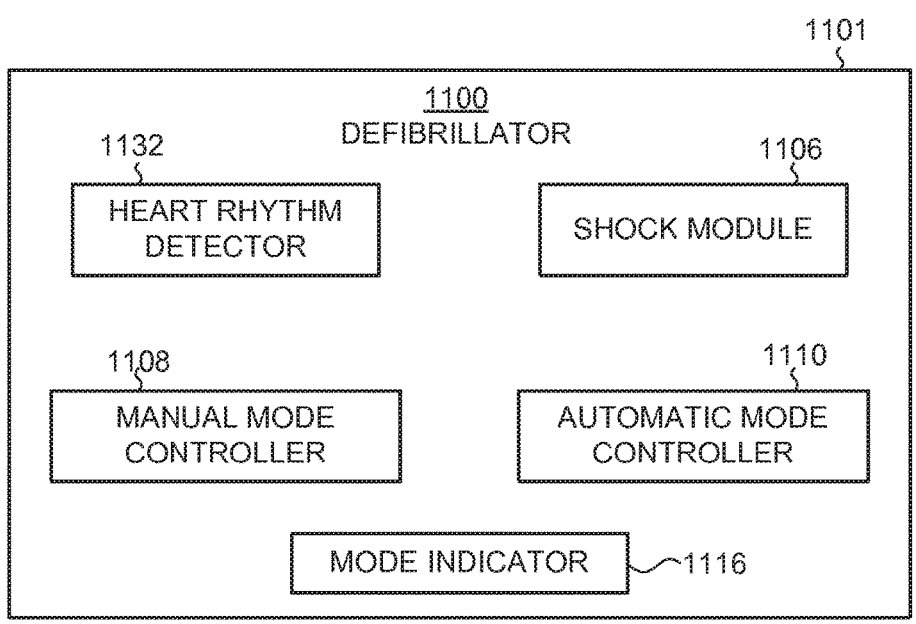
FIG. 11  *DEFIBRILLATOR WITH MODE INDICATOR*

*DEFIBRILLATOR WITH USER INTERFACE*

*METHOD OF OPERATING EXTERNAL DEFIBRILLATOR IN DIFFERENT OPERATIONAL MODES*

INTELLIGENT SYNCH MODE FOR DEFIBRILLATION

CROSS REFERENCE TO RELATED APPLICATIONS

The present application is continuation application of U.S. patent application Ser. No. 13/835,261 filed Mar. 15, 2013 which claims priority to U.S. Provisional Patent Application Ser. No. 61/707,435 filed Sep. 28, 2012. The entire disclosure contents of these applications are herewith incorporated by reference into the present application.

FIELD

This invention generally relates to external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrhythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively.

External defibrillators are used not only to treat victims of sudden cardiac arrest experiencing VF, but also for cardioversion of other tachyarrhythmias (such as atrial fibrillation) that may be experienced by a person not in cardiac arrest. For purposes of both defibrillation and cardioversion, most manual defibrillators provide a button or similar control for the rescuer to cause the device to administer an electric shock through the heart of the patient. For purposes of cardioversion, however, it is frequently important to precisely time the delivery of the shock relative to the patient's intrinsic heart rhythm, so that the shock does not inadvertently exacerbate the situation and cause the patient's condition to worsen, perhaps resulting in ventricular fibrillation. Such timing is extremely difficult or impossible for a defibrillator user to achieve based upon their own observation of the ECG rhythm and physical ability to push the shock button at the precise desired time.

Manual defibrillators, and some Automated External Defibrillators (AEDs), may therefore provide a sync (or synchronization) function that, upon activation, automatically adjusts the timing of shock delivery to be coincident (e.g., not simultaneous with the QRS complex, but with a fixed delay) with the next detected QRS complex or R wave in the monitored ECG signal in order to avoid delivering the shock during the T wave, which may result in the initiation of VF by stimulating during the vulnerable period. So, when this button is pushed, the defibrillator waits for the optimum instant (based upon the QRS complex or R wave of the monitored ECG signal) and then causes the shock to be delivered at that instant. This defibrillator operating mode is frequently called synchronized shock mode, or sync mode. When the defibrillator is not in this synchronized shock operating mode, it is in asynchronous shock mode.

While synchronized cardioversion is a common procedure, it is also fraught with user error. For example, the user may forget or ignore how the device is configured to behave after delivery of an initial synchronized shock. Also, even manual defibrillators that are configured to remain in sync mode or return to asynchronous mode after a synchronized discharge can create a hazard. For example, if the user is unaware or inattentive to the fact that the device is configured to return to asynchronous mode and the patient requires another synchronized shock, the user may inadvertently deliver an asynchronous shock, which could potentially trigger ventricular fibrillation. On the other hand, if the user is unaware or inattentive to the fact that the device is configured to remain in sync mode and the patient develops a pulseless tachyarrhythmia requiring an asynchronous shock, the user will not be able to deliver the necessary therapy until he or she recognizes that the device is still in sync mode and they manually deactivate the sync function.

In an automated device such as an AED or a wearable cardioverter/defibrillator, the device may only have an automatic mode in which it automatically determines what shocking mode to use (e.g., synchronous versus asynchronous) based on the monitored ECG signal. There would generally not be a default synchronization mode in the device configuration; instead, the synchronization mode would be based on the monitored ECG signal. Furthermore, in situations where the rhythm identified from the monitored ECG signal hovers between arrhythmias that require either synchronous or asynchronous shock, the device may have a programmable setting to configure a smart algorithm to either require at least 30 seconds of continuous detection before switching synchronization mode, or have a voting schema that uses multiple ECG segments.

For the wearable device, the shock recipient (e.g., patient) may be involved in the selection of the sync mode by providing input on his condition (e.g., by saying "I am awake" for synchronizing the shock).

BRIEF SUMMARY

The present description gives instances of medical devices, systems, software and methods, the use of which may help overcome problems and limitations of the prior art.

In one embodiment, an external defibrillator, such as a manual defibrillator, AED, or wearable defibrillator, includes a housing, a heart rhythm detector structured to detect the heart rhythm of a patient, a manual mode controller structured to set the defibrillator in a synchronous shock operating mode or an asynchronous shock operating mode depending on an input from a human operator, a shock module located within the housing and configured to cause the defibrillator to deliver the shock to the patient according to the operating mode of the defibrillator, and an automatic mode controller structured to, after the shock module has delivered the shock to the patient, set the external defibrillator to the synchronous shock operating mode or the asynchronous shock operating mode depending on the detected heart rhythm of the patient and without input from the human operator.

An advantage over the prior art is that such defibrillator reduces the potential for user confusion and error associated with the sync function by incorporating an automated algorithm to intelligently determine the behavior of the device surrounding delivery of a synchronized shock.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 10 is a block diagram of a defibrillator having a processor that includes the shock module.

FIG. 11 is a block diagram of a defibrillator having a mode indicator that signals the operational mode of the defibrillator.

DETAILED DESCRIPTION

Figure 3:
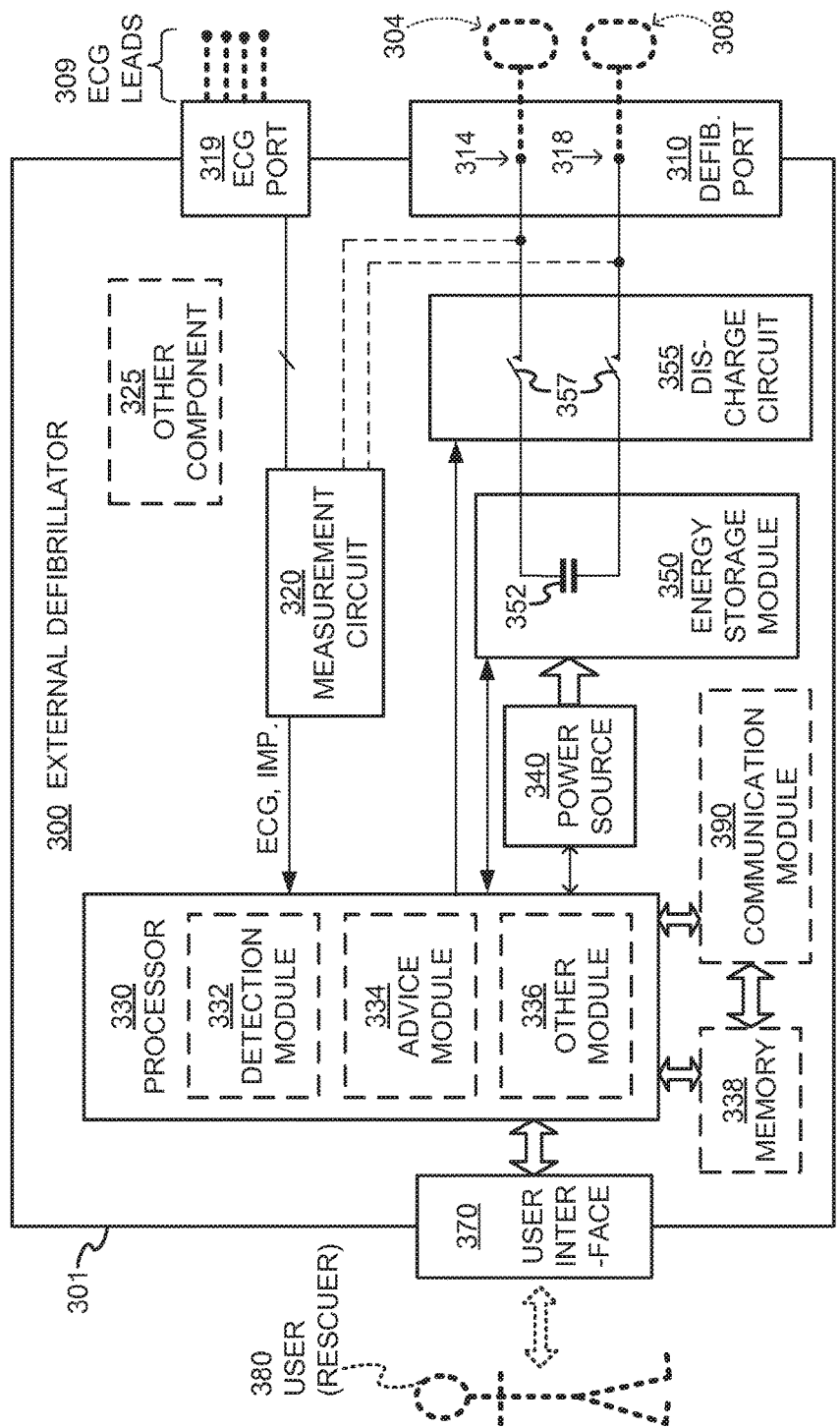
FIG. 3 is a diagram showing components of an external defibrillator, such as the one shown in FIG. 1, which is made according to embodiments.

As has been mentioned, the present description is about medical devices, methods of operating such medical devices, and a programmed processor to control such medical devices for controlling enabling features of the medical device based on setting a sync mode according to an input by a human, defibrillating pursuant to the sync mode and, after the defibrillating, receiving the patient's ECG and setting the sync mode automatically based on the ECG and without additional human input.

Embodiments are now described in more detail.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and an other component 325 for the above described additional features, such as patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Component 325 can be a heart rhythm detector, as will be appreciated by the following description, except perhaps if such a heart rhythm detector has been implemented as measurement circuit 320. Alternately, component 325 can be a manual mode controller or an automatic mode controller as will be appreciated by the following description, except perhaps if such controllers have been implemented within processor 330.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

A feature of a defibrillator can be CPR-prompting. Prompts are issued to the user, visual or by sound, so that the user can administer CPR. Examples are taught in U.S. Pat. Nos. 6,334,070 and 6,356,785.

Figure 4:
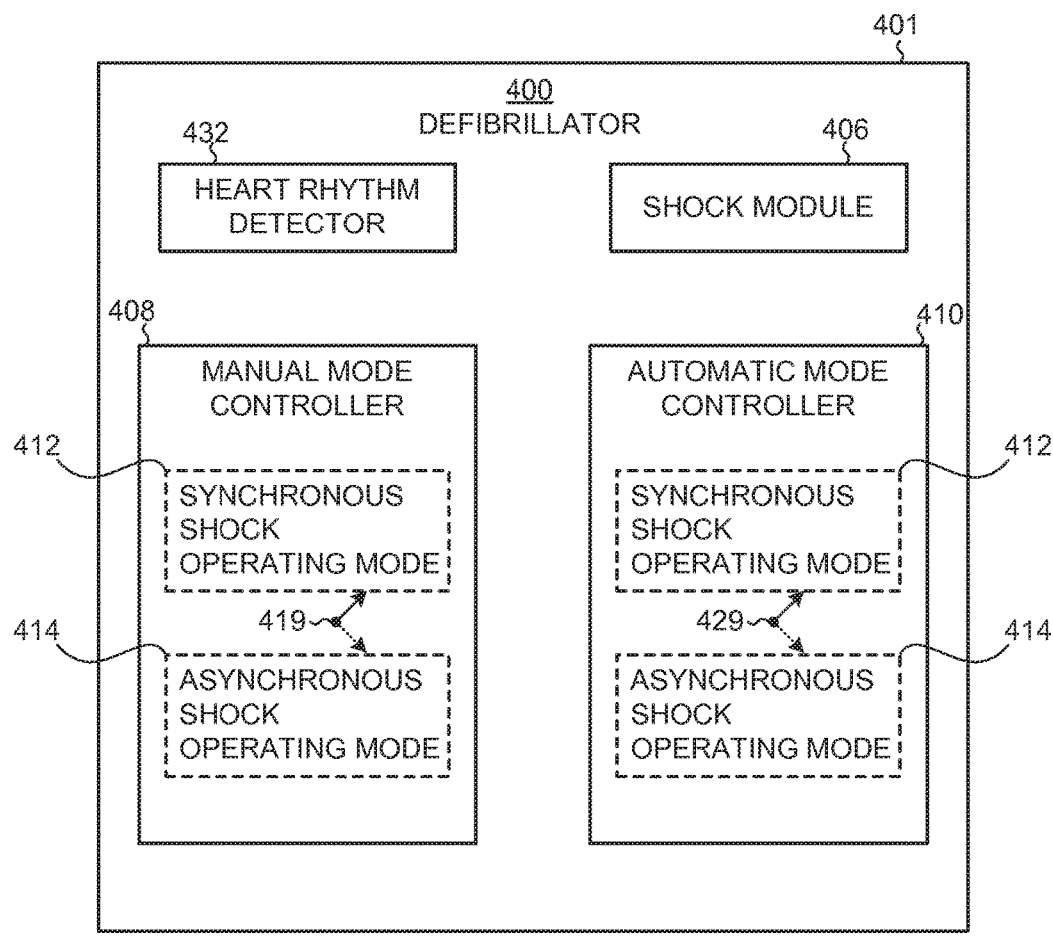
FIG. 4 is a block diagram of a defibrillator having a heart rhythm detector, a manual mode controller, and an automatic mode controller.

FIG. 4 is a block diagram of a defibrillator 400 having a housing 401, a heart rhythm detector 432 structured to detect the heart rhythm of the patient, a shock module 406, a manual mode controller 408, and an automatic mode controller 410. The defibrillator 400 has a synchronous shock operating mode 412 in which delivery of a shock to a patient is timed to be coincident with a certain QRS complex in the heart rhythm of the patient, and an asynchronous shock operating mode 414 distinct from the synchronous operating mode 412 in which delivery of the shock is timed independent of the certain QRS complex in the heart rhythm of the patient.

The manual mode controller 408 may be structured to set the defibrillator 400 in the synchronous shock operating mode 412 or the asynchronous shock operating mode 414, as indicated by 419, depending on an input from a human operator. The input can be a manual input, voice input, or other suitable input transmitted by a human operation. As used herein, the term human operation generally refers to a rescuer, bystander, or the patient, when conscious and/or attached to a wearable defibrillator, for example. The shock module 406 is located within the housing 401 and may be configured to cause the defibrillator 400 to deliver the shock to the patient according to the operating mode of the defibrillator 400. The automatic mode controller 410 may be structured to, after the shock module 406 has delivered the shock to the patient, set the defibrillator 400 to the synchronous shock operating mode 412 or the asynchronous shock operating mode 414, as indicated by 429, depending on the detected heart rhythm of the patient and without input from the human operator.

In certain embodiments, the automatic mode controller 410 may cause the defibrillator 400 to operate in synchronous shock operating mode 412 after the shock module 406 delivers the shock to the patient unless a heart rhythm meriting delivery of an asynchronous shock (hereinafter referred to as an "asynchronous shock heart rhythm") is detected in the patient after the shock has been delivered. When the asynchronous shock heart rhythm is detected in the patient after the shock is delivered, the automatic mode controller 410 may cause the defibrillator 400 to operate in the asynchronous shock operating mode 414. The automatic mode controller 410 may cause the defibrillator 400 to automatically operate in the asynchronous shock mode 412 when the asynchronous shock heart rhythm is detected in the patient.

The heart rhythm detector 432 may be configured to analyze the heart rhythm of the patient before the shock is delivered to the patient by the shock module 406. The heart rhythm detector 432 may be further configured to analyze the heart rhythm of the patient before the shock is delivered to the patient to identify an asynchronous shock heart rhythm and to cause the automatic mode controller 410 to set or maintain the defibrillator 400 in the asynchronous shock operating mode 414 when the asynchronous shock heart rhythm is detected in the patient.

In certain embodiments, the heart rhythm detector 432 may be structured to detect the heart rhythm of the patient both before and after the shock is delivered to the patient. When the heart rhythm detector 432 detects that the detected heart rhythm of the patient is an asynchronous heart rhythm before or after the shock is delivered to the patient, the automatic mode controller 410 may be structured to set or maintain the defibrillator in the asynchronous shock mode. Alternatively or in addition thereto, the heart rhythm detector 432 may be structured to detect the heart rhythm of the patient multiple times after the shock has been delivered to the patient.

In certain embodiments, the automatic mode controller 410 may be structured to set or maintain the defibrillator 400 in the synchronous shock mode 412 after the shock is delivered to the patient only when the detected ECG of the patient includes a QRS complex. In such embodiments, the automatic mode controller 410 may be structured to set or maintain the defibrillator 400 in the asynchronous shock mode 414 after the shock is delivered to the patient when the detected ECG of the patient is an asynchronous shock heart rhythm.

Figure 5:
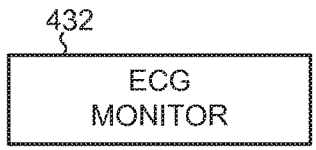
FIG. 5 is a block diagram in which the heart rhythm detector shown in FIG. 4 is an ECG monitor.

FIG. 5 is a block diagram in which the heart rhythm detector 432 shown in FIG. 4 is an electrocardiogram (ECG) monitor. In such embodiments, the heart rhythm detector 432 is structured to detect at least an ECG of the patient to determine the heart rhythm of the patient and the automatic mode controller is structured to set or maintain the defibrillator in the synchronous shock operating mode after the shock has been delivered to the patient when the detected ECG of the patient includes a QRS complex after the shock has been delivered to the patient.

Figure 6:
FIG. 6 is a block diagram in which the heart rhythm detector shown in FIG. 4 is a blood pressure monitor.

FIG. 6 is a block diagram in which the heart rhythm detector 432 shown in FIG. 4 is a blood pressure monitor. In such embodiments, the heart rhythm detected by the heart rhythm detector 432 includes a detection of the blood pressure of the patient. The automatic mode controller may be structured to set or maintain the defibrillator in the asynchronous shock mode if the detected blood pressure of the patient is consistent with a heart rhythm meriting an asynchronous shock (hereinafter referred to as an "asynchronous shock blood pressure"). For example, an absence of pulsatile blood pressure might indicate an asynchronous shock is merited. Alternatively or in addition thereto, the automatic mode controller may be structured to set or maintain the defibrillator in the synchronous shock mode if the detected blood pressure of the patient is consistent with a heart rhythm meriting a synchronous shock (hereinafter referred to as a "synchronous shock blood pressure").

Figure 7:
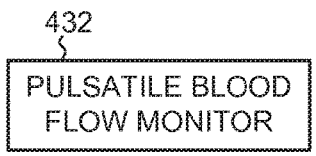
FIG. 7 is a block diagram in which the heart rhythm detector shown in FIG. 4 is a pulsatile blood flow monitor.

FIG. 7 is a block diagram in which the heart rhythm detector 432 shown in FIG. 4 is a pulsatile blood flow monitor. In such embodiments, the heart rhythm detected by the heart rhythm detector 432 includes the pulsatile blood flow of the patient. The heart rhythm detector 432 may be structured to detect the pulsatile blood flow of the patient with at least one of a pulse oximeter and a Doppler ultrasound sensor. The automatic mode controller may be structured to set or maintain the defibrillator in the synchronous shock mode if the detected pulsatile blood flow of the patient is consistent with a heart rhythm meriting a synchronous shock (hereinafter referred to as a "synchronous shock pulsatile blood flow"). Alternatively or in addition thereto, the automatic mode controller may be structured to set or maintain the defibrillator in the asynchronous shock mode if the detected pulsatile blood flow of the patient is consistent with a heart rhythm meriting an asynchronous shock (hereinafter referred to as an "asynchronous shock pulsatile blood flow"). For example, an absent pulsatile blood flow, a low amplitude pulsatile blood flow, or a sudden change to a much smaller amplitude pulsatile blood flow might indicate that an asynchronous shock is merited.

For a wearable defibrillator (WCD), another detector may be input provided by the patient as an indicator that the patient is awake and conscious and able to operate the WCD. The device may query the patient, e.g., by asking "are you awake", and, if the patient responds in the affirmative (e.g., by providing input via a user interface), the defibrillator may remain in synchronous mode. If there is conflict between the monitored ECG signal rhythm identification and the patient input mode, however, the device may take the patient input and wait for a fixed period of time (e.g., a 30-second interval), before making another assessment of synchronous mode change. In certain embodiments, the interval may have a value that is less than a single second, e.g., measured in milliseconds, or even zero seconds.

Figure 8:
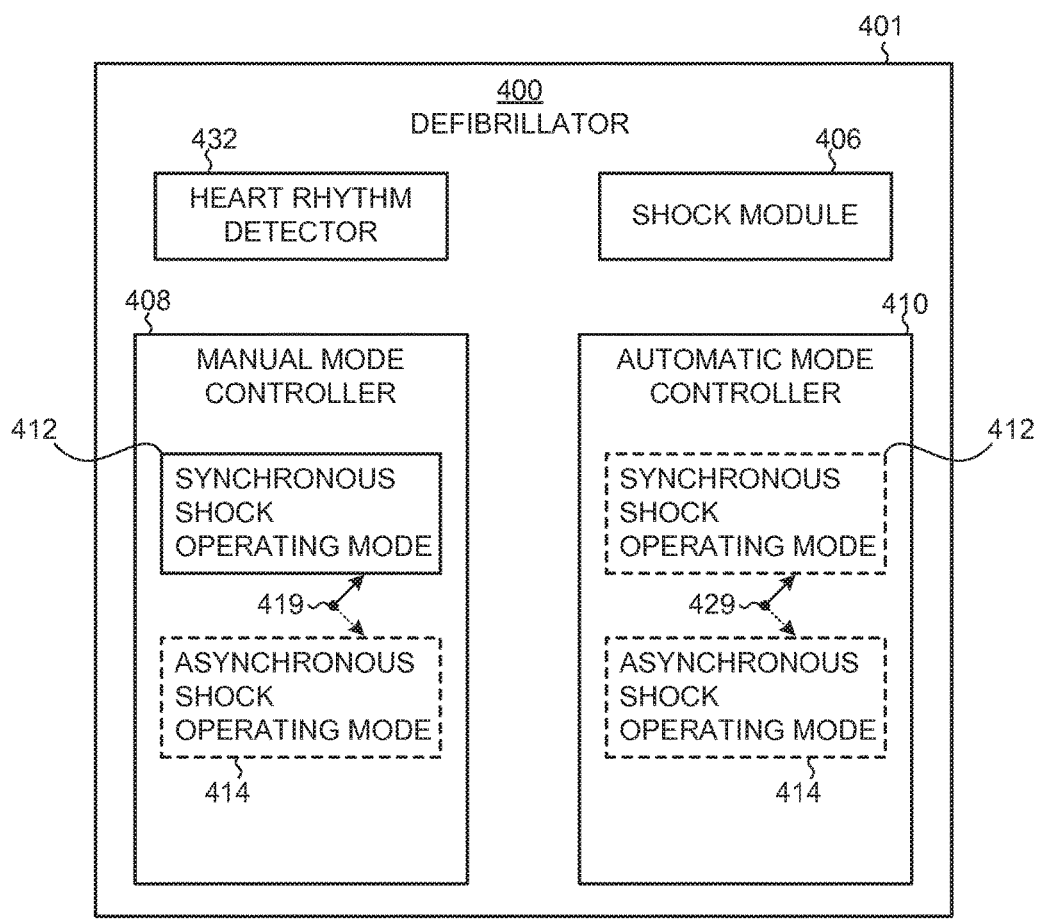
FIG. 8 is a block diagram of the defibrillator shown in FIG. 4 having a manual mode controller with a default operating mode that is a synchronous shock operating mode.

FIG. 8 is a block diagram of the defibrillator 400 shown in FIG. 4 having a manual mode controller 408 with a default operating mode that is a synchronous shock operating mode 412, as compared to the defibrillator 400 shown in FIG. 4 in which the manual mode controller 408 does not necessarily have a default operating mode that is the synchronous shock operating mode 412.

Figure 9:
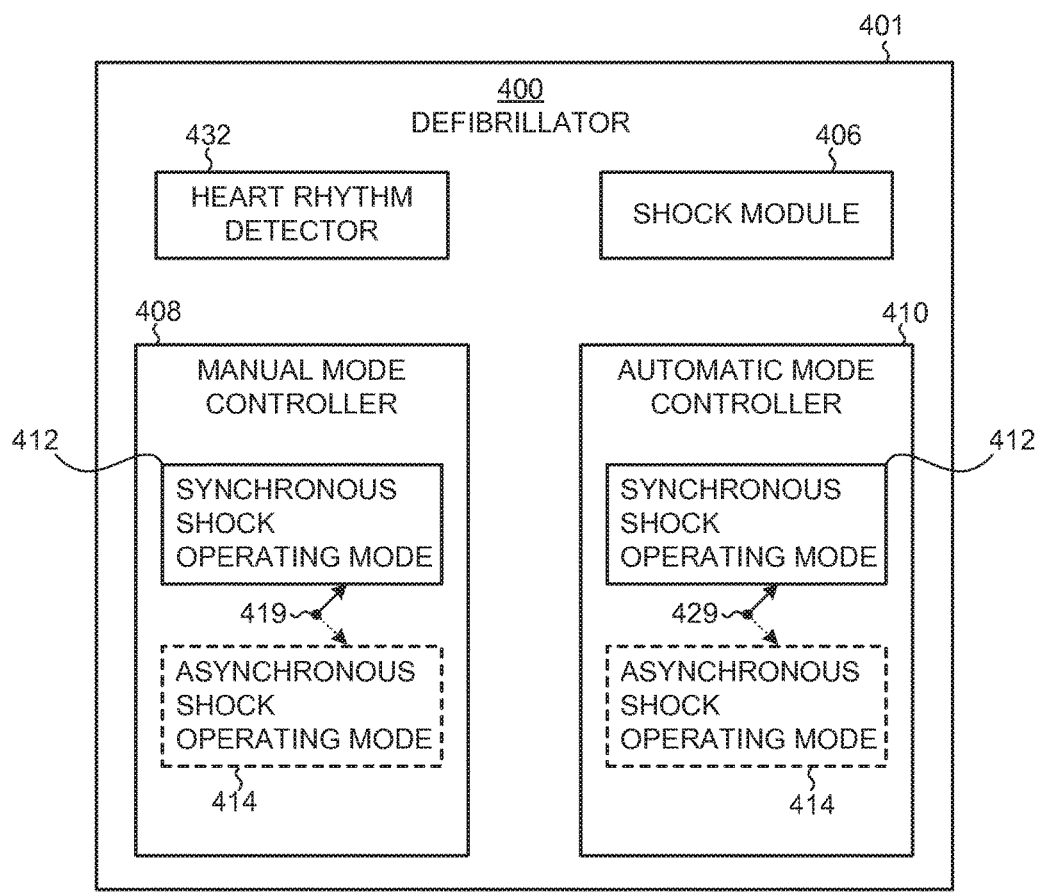
FIG. 9 is a block diagram of the defibrillator shown in FIG. 4 having a manual mode controller and an automatic mode controller in which the default operating mode is synchronous shock operating mode for both the manual mode controller and the automatic mode controller.

FIG. 9 is a block diagram of the defibrillator 400 shown in FIG. 4 having a manual mode controller 408 and an automatic mode controller 410 in which the default operating mode is synchronous shock operating mode 412 for both the manual mode controller 408 and the automatic mode controller 410. In such embodiments, the automatic mode controller 408 may be structured to set or maintain the defibrillator 400 in the synchronous shock mode 412 after the shock is delivered to the patient for a certain interval.

FIG. 10 is a block diagram of a defibrillator 1000 having a housing 1001 and a heart rhythm detector 1032, shock module 1006, manual mode controller 1008, and automatic mode controller 1010 within the housing 1001. In the example, the defibrillator 1000 further includes a processor 1030 that includes the automatic mode controller 1010.

FIG. 11 is a block diagram of a defibrillator 1100 having a housing 1101 and a heart rhythm detector 1132, shock module 1106, manual mode controller 1108, and automatic mode controller 1110 within the housing 1101. In the example, the defibrillator 1100 further includes a mode indicator 1116 that signals the operating mode of the defibrillator 1100. In certain embodiments, the mode indicator 1116 is audible. Alternatively or in addition thereto, the mode indicator 1116 is visual.

Figure 12:
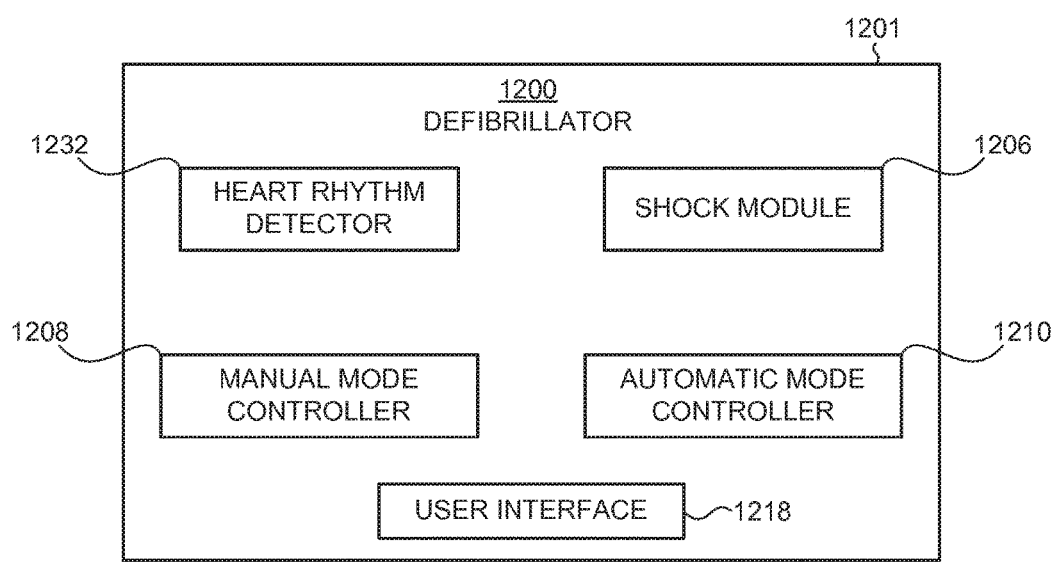
FIG. 12 is a block diagram of a defibrillator having a user interface.

FIG. 12 is a block diagram of a defibrillator 1200 having a housing 1201 and a heart rhythm detector 1232, shock module 1206, manual mode controller 1208, and automatic mode controller 1210 within the housing 1201. In the example, the defibrillator 1200 further includes a user interface 1218. The user interface 1218 may be configured to prompt the user at the end of the interval described above with regard to FIG. 9 in order to set the operating mode of the defibrillator 1200, for example. Such prompting may include visual and/or audible content, for example. In alternative embodiments, some of the individual components of the defibrillator 1200 (e.g., the manual mode controller 1208 and/or automatic mode controller 1210) may be situated or positioned outside the housing 1201 (e.g., physically separate from the other components of the defibrillator 1200).

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

Figure 13:
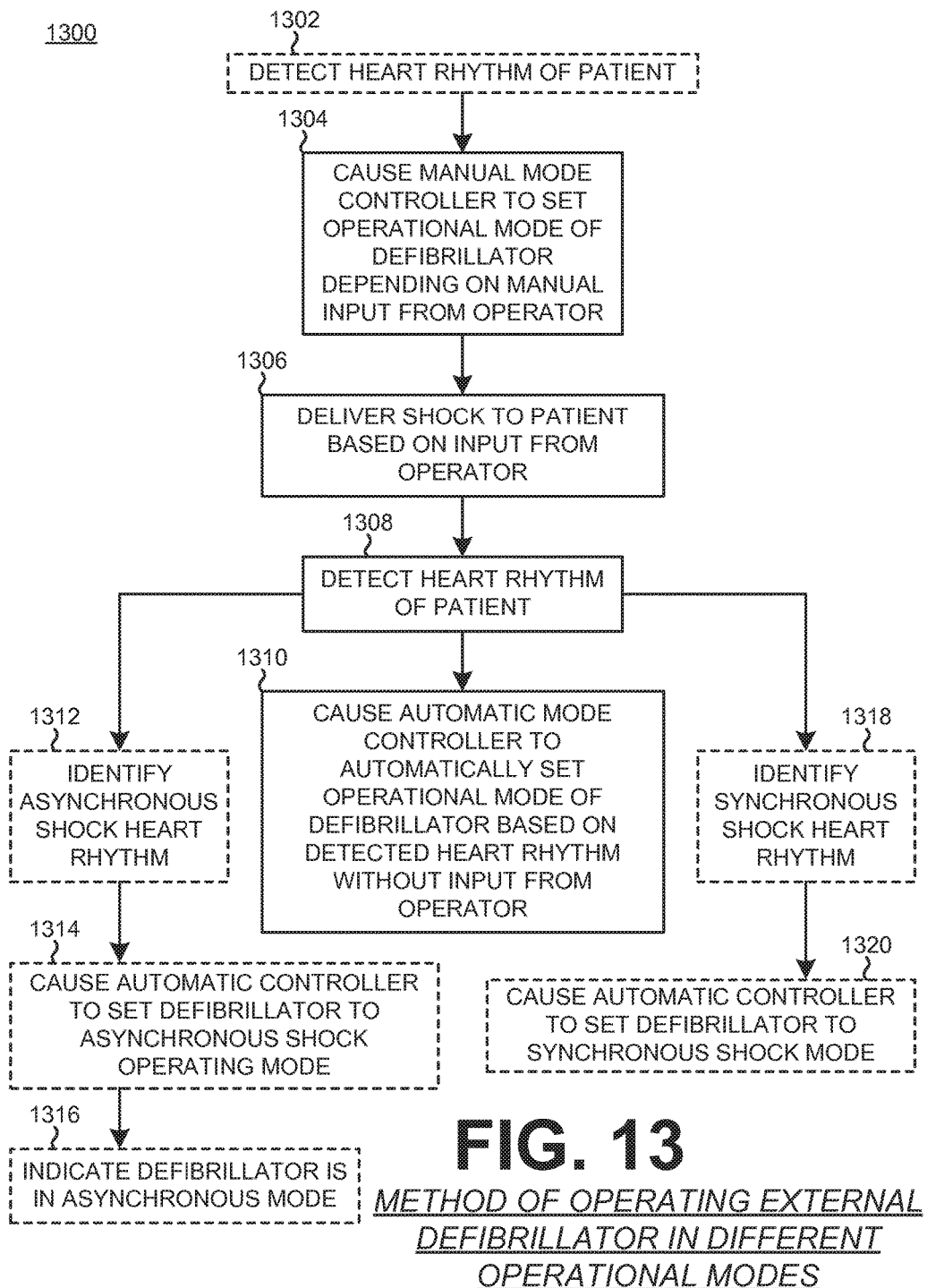
FIG. 13 is a flowchart for illustrating methods according to embodiments.

FIG. 13 is a flowchart 1300 for illustrating methods according to embodiments. Such methods are generally directed to operating an external defibrillator having a synchronous shock operating mode in which delivery of a shock to a patient is timed to be coincident with a certain QRS complex in a heart rhythm of the patient, and an asynchronous shock operating mode distinct from the synchronous operating mode in which delivery of the shock is timed independent of the certain QRS complex in the heart rhythm of the patient.

According to an optional operation 1302, the heart rhythm of the patient is detected before the delivery of the shock to the patient. In certain embodiments, detecting the heart rhythm of the patient may include detecting the electrocardiogram (ECG) of the patient. Alternatively or in addition thereto, detecting the heart rhythm of the patient may include detecting the blood pressure of the patient. Alternatively or in addition thereto, detecting the heart rhythm of the patient may include detecting the pulsatile blood flow of the patient.

According to an operation 1304, a manual mode controller is caused to set the external defibrillator to operate in the synchronous shock operating mode or the asynchronous shock operating mode depending on an input from a human operator.

According to an operation 1306, the shock is delivered to the patient based on the manual input.

According to an operation 1308, the heart rhythm of the patient is detected after the delivery of the shock to the patient. In certain embodiments, detecting the heart rhythm of the patient after delivering the shock includes detecting the heart rhythm of the patient multiple times.

According to an operation at 1310, an automatic mode controller is caused to automatically set the defibrillator to operate in the synchronous shock mode or the asynchronous shock mode based on the detected heart rhythm of the patient without input from the human operator. In certain embodiments, the automatic mode controller may be caused to automatically set the defibrillator to operate in the synchronous shock operating mode after the shock is delivered unless the detected heart rhythm of the patient includes an asynchronous shock heart rhythm. Alternatively or in addition thereto, the automatic mode controller may be caused to automatically set the defibrillator to operate in the synchronous shock operating mode if the detected heart rhythm of the patient includes an R-wave.

Alternatively or in addition thereto, the automatic mode controller may be caused to set the defibrillator to operate either the synchronous shock operating mode or the asynchronous shock operating mode for an interval after delivering shock. Such an interval may include a period of time beginning after the shock is delivered. This interval may range anywhere from approximately 10 seconds to approximately 5 minutes, for example. In certain embodiments, the interval may have a value that is less than a single second, e.g., measured in milliseconds, or even zero seconds. A human operator may be prompted to cause the manual mode controller to set the defibrillator to operate in the synchronous shock operating mode or the asynchronous shock operating mode at the end of the interval. Should the user fail to cause the manual mode controller to set the defibrillator to operate in the synchronous shock operating mode or the asynchronous shock operating mode at the end of the interval, the automatic mode controller may be caused to automatically set the defibrillator to operate in the asynchronous shock operating mode.

According to an optional operation at 1312, an asynchronous shock heart rhythm of the patient may be identified. According to a next optional operation at 1314, the automatic mode controller is caused to set the defibrillator to operate in the asynchronous shock operating mode. In certain embodiments, the automatic mode controller is caused to automatically set the defibrillator to operate in the asynchronous shock operating mode.

According to an optional operation at 1316, an indication that the defibrillator is operating in the asynchronous shock operating mode may be provided. Alternatively or in addition thereto, an asynchronous shock may be delivered to the patient. Indicating that the defibrillator is operating in the asynchronous shock operating mode may include audibly indicating that the defibrillator is operating in the asynchronous shock operating mode.

According to an optional operation at 1318, a synchronous shock heart rhythm of the patient may be identified. According to a next optional operation at 1320, the automatic mode controller is caused to set the defibrillator to operate in the synchronous shock operating mode. In certain embodiments, the automatic mode controller is caused to automatically set the defibrillator to operate in the synchronous shock operating mode.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

What is claimed is:

1. A defibrillator comprising:
    a plurality of operating modes including a synchronous shock operating mode and an asynchronous shock operating mode;
    a heart rhythm detector that detects the heart rhythm of a shock recipient;
    a manual mode controller that sets the defibrillator in the synchronous shock operating mode or the asynchronous shock operating mode;
    a shock module that causes the defibrillator to deliver a shock to the shock recipient according to the operating mode of the defibrillator; and
    an automatic mode controller that sets the defibrillator to the synchronous shock operating mode or the asynchronous shock operating mode depending on the detected heart rhythm of the shock recipient.

2. The defibrillator of claim 1, in which
    the manual mode controller sets the defibrillator in the synchronous shock operating mode depending on an input.

3. The defibrillator of claim 1, in which
    the manual mode controller sets the defibrillator in the asynchronous shock operating mode depending on an input.

4. The defibrillator of claim 2, wherein
    the input comprises an input from an operator of the defibrillator.

5. The defibrillator of claim 1, wherein
    the automatic mode controller sets the defibrillator after the defibrillator has delivered a shock.

6. The defibrillator of claim 1, wherein
the automatic mode controller sets the defibrillator after the defibrillator has delivered a shock.

7. The defibrillator of claim 1, wherein
the automatic mode controller sets the defibrillator to the synchronous shock operating mode without an input from an operator.

8. The defibrillator of claim 7, wherein
the automatic mode controller sets the defibrillator to the synchronous shock operating mode without an input from the shock recipient.

9. The defibrillator of claim 8, wherein
the input from shock recipient is representative of a condition of the shock recipient.

10. The defibrillator of claim 1, wherein
the automatic mode controller sets the defibrillator to the asynchronous shock operating mode without an input from an operator.

11. The defibrillator of claim 10, wherein
the automatic mode controller sets the defibrillator to the synchronous shock operating mode without an input from the shock recipient.

12. The defibrillator of claim 11, wherein
the input from the shock recipient is representative of a condition of the shock recipient.

13. The defibrillator of claim 1, wherein
the synchronous shock operating mode operates to deliver a shock that is timed to correlate with a certain QRS complex in a heart rhythm.

14. The defibrillator of claim 1, wherein
the asynchronous shock operating mode is distinct from the synchronous operating mode in which delivery of a shock is timed independent of a certain QRS complex in a heart.

15. The defibrillator of claim 14, wherein
the heart rhythm detector detects at least one of an electrocardiogram (ECG) or a pulsatile blood flow monitor to determine the heart rhythm.

16. The defibrillator of claim 15, in which
the automatic mode controller sets the defibrillator in the synchronous shock operating mode after the shock has been delivered,
when the detected ECG includes a QRS complex after the shock has been delivered.

17. The defibrillator of claim 1, further comprising:
a processor that includes the automatic mode controller.

18. The defibrillator of claim 1, wherein
the defibrillator comprises an external defibrillator.

19. The defibrillator of claim 1, wherein
the heart rhythm detector detects the heart rhythm of the shock recipient a plurality of times after the shock has been delivered to the shock recipient.

20. The defibrillator of claim 1, wherein
the heart rhythm detector analyzes the heart rhythm of the shock recipient before a shock is delivered.

* * * * *